(12) United States Patent
Zimmermann et al.

(10) Patent No.: US 6,868,350 B2
(45) Date of Patent: Mar. 15, 2005

(54) METHOD AND APPARATUS FOR THE DETECTION OF THE RESPONSE OF A SENSING DEVICE

(75) Inventors: Bernd D. Zimmermann, Ashland, OH (US); Prasad S. Khadkikar, Lexington, OH (US); Lance A. Bostic, Ashland, OH (US)

(73) Assignee: Therm-O-Disc, Incorporated, Mansfield, OH (US)

( * ) Notice: Subject to any disclaimer, the term of this patent is extended or adjusted under 35 U.S.C. 154(b) by 62 days.

(21) Appl. No.: 10/411,894

(22) Filed: Apr. 11, 2003

(65) Prior Publication Data

US 2004/0204920 A1 Oct. 14, 2004

(51) Int. Cl.[7] .............................................. G06F 19/00
(52) U.S. Cl. ........................ 702/65; 702/116; 702/189; 702/193
(58) Field of Search .............................. 702/45, 53, 57, 702/65, 79, 116, 193, 189; 73/204.22, 204.25, 204.27; 205/775, 782.5, 787

(56) References Cited

U.S. PATENT DOCUMENTS

| | | | |
|---|---|---|---|
| 4,004,452 A | 1/1977 | Logothetis et al. | |
| 4,423,407 A | 12/1983 | Zuckerman | |
| 4,472,356 A | 9/1984 | Kolesar, Jr. | |
| 4,631,952 A | 12/1986 | Donaghey | |
| 4,642,601 A | 2/1987 | Sugawara et al. | |
| 4,988,970 A | 1/1991 | Hafele | |
| 5,515,723 A | 5/1996 | Tsuchida et al. | |
| 5,789,659 A | 8/1998 | Williams | |
| 5,911,872 A | * 6/1999 | Lewis et al. | ................. 205/787 |
| 6,055,849 A | 5/2000 | Shioiri et al. | |
| 6,387,329 B1 | * 5/2002 | Lewis et al. | ................... 422/98 |
| 6,435,003 B1 | 8/2002 | Warburton | |

FOREIGN PATENT DOCUMENTS

FR 2751413 1/1998
WO WO 97/01753 1/1997

OTHER PUBLICATIONS

Communication, including European Search Report, from the European Patent Office, Aug. 5, 2004.

* cited by examiner

Primary Examiner—Bryan Bui
(74) Attorney, Agent, or Firm—Harness, Dickey & Pierce, PLC

(57) ABSTRACT

A method for operating a sensing device. The method comprising: a sensor film having an electrical resistance that is adapted to change in response to the presence of a predetermined condition; detecting the presence of the predetermined condition; measuring the electrical resistance of the sensor film at a first time; measuring the electrical resistance of the sensor film at a second time; determining a rate of change of the electrical resistance between the first time and the second time; and comparing the rate of change of the electrical resistance against a threshold value.

48 Claims, 8 Drawing Sheets

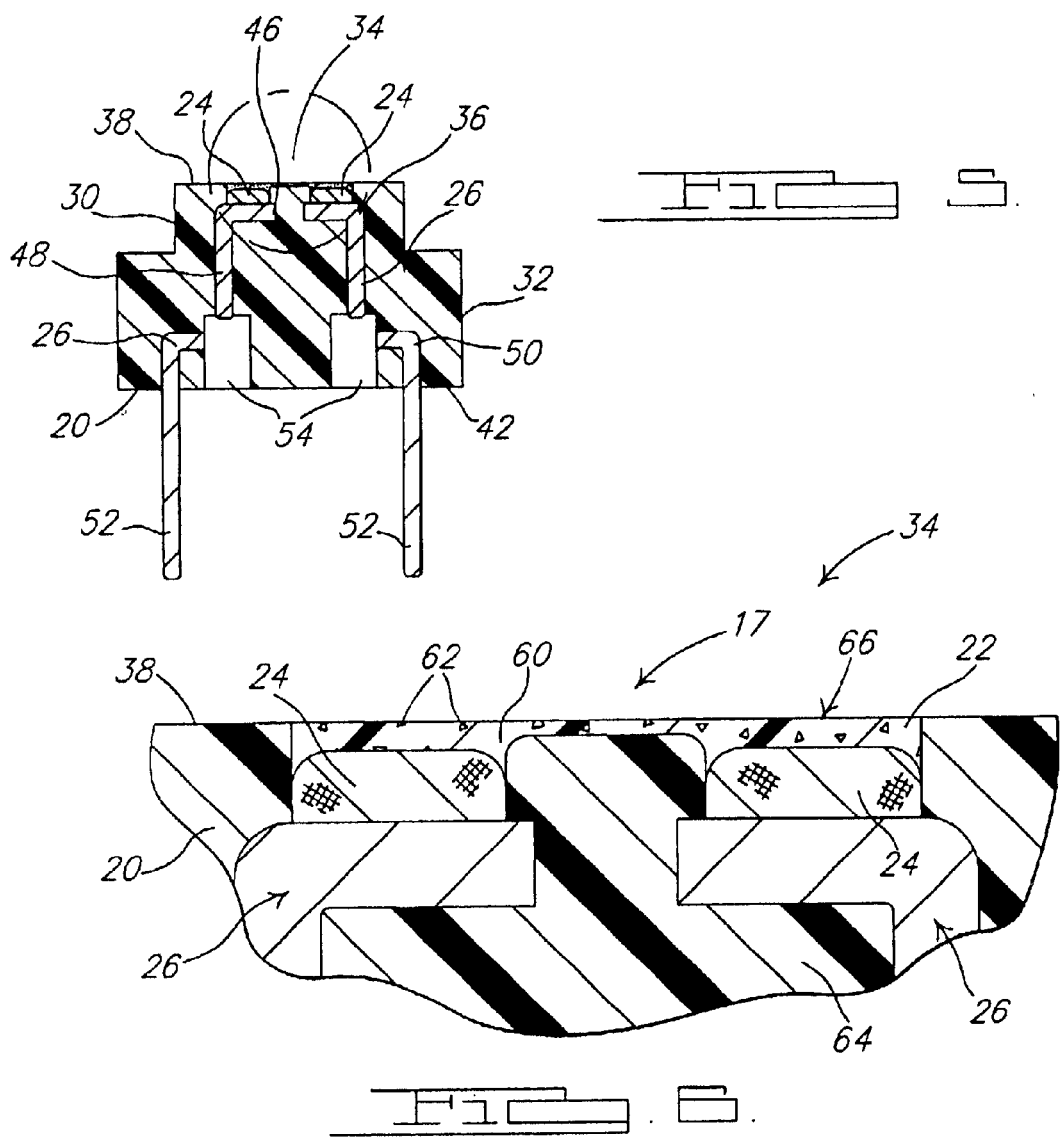
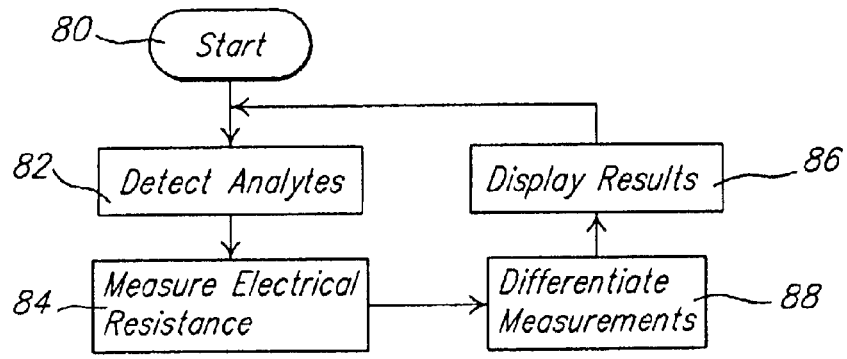

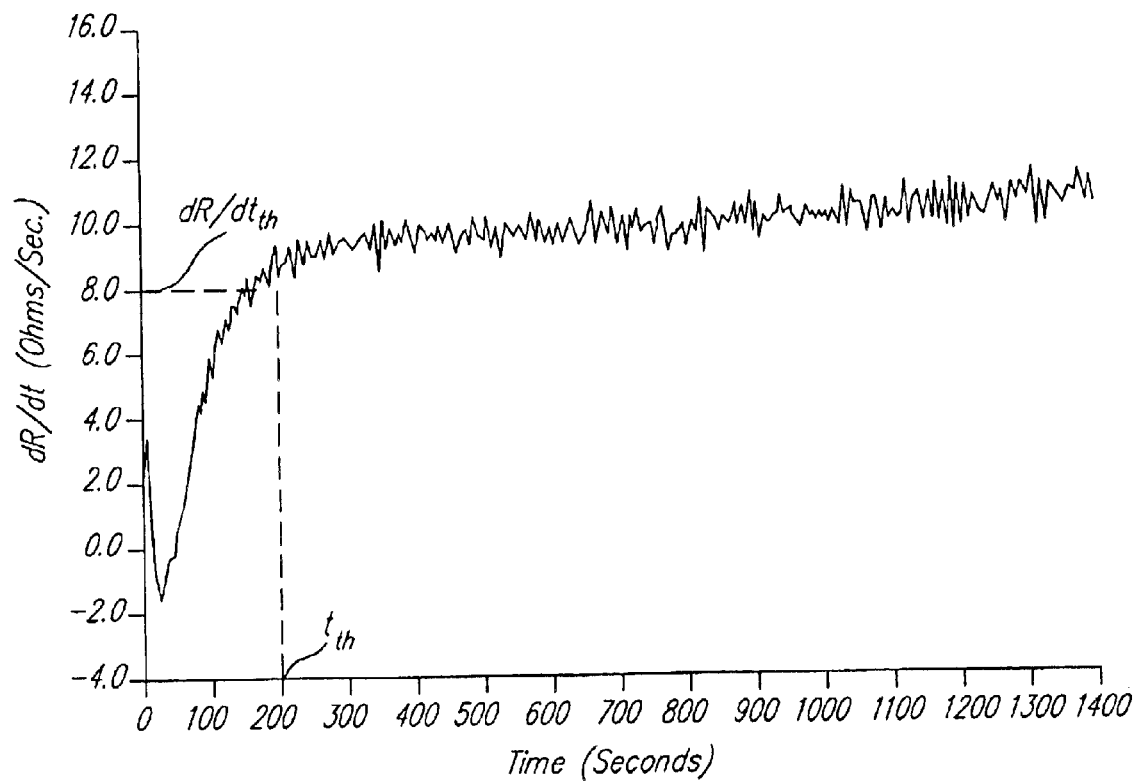
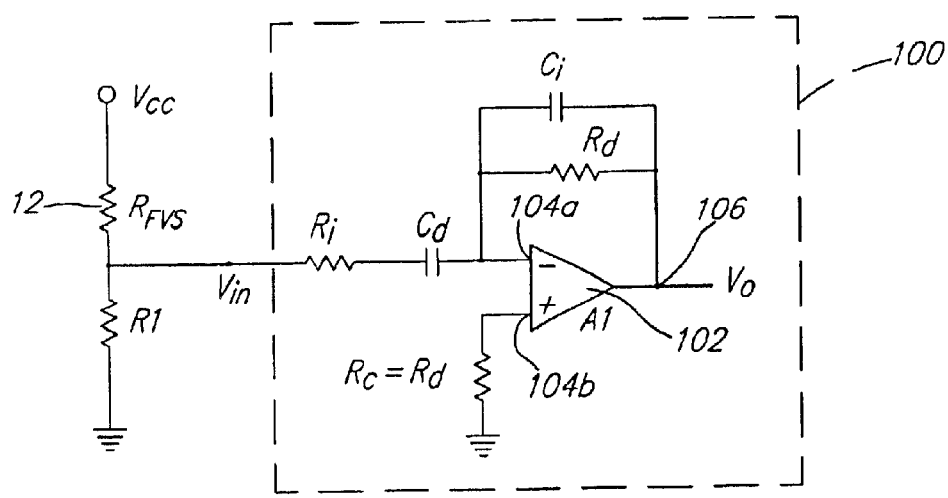
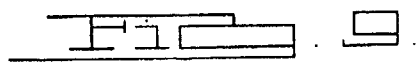

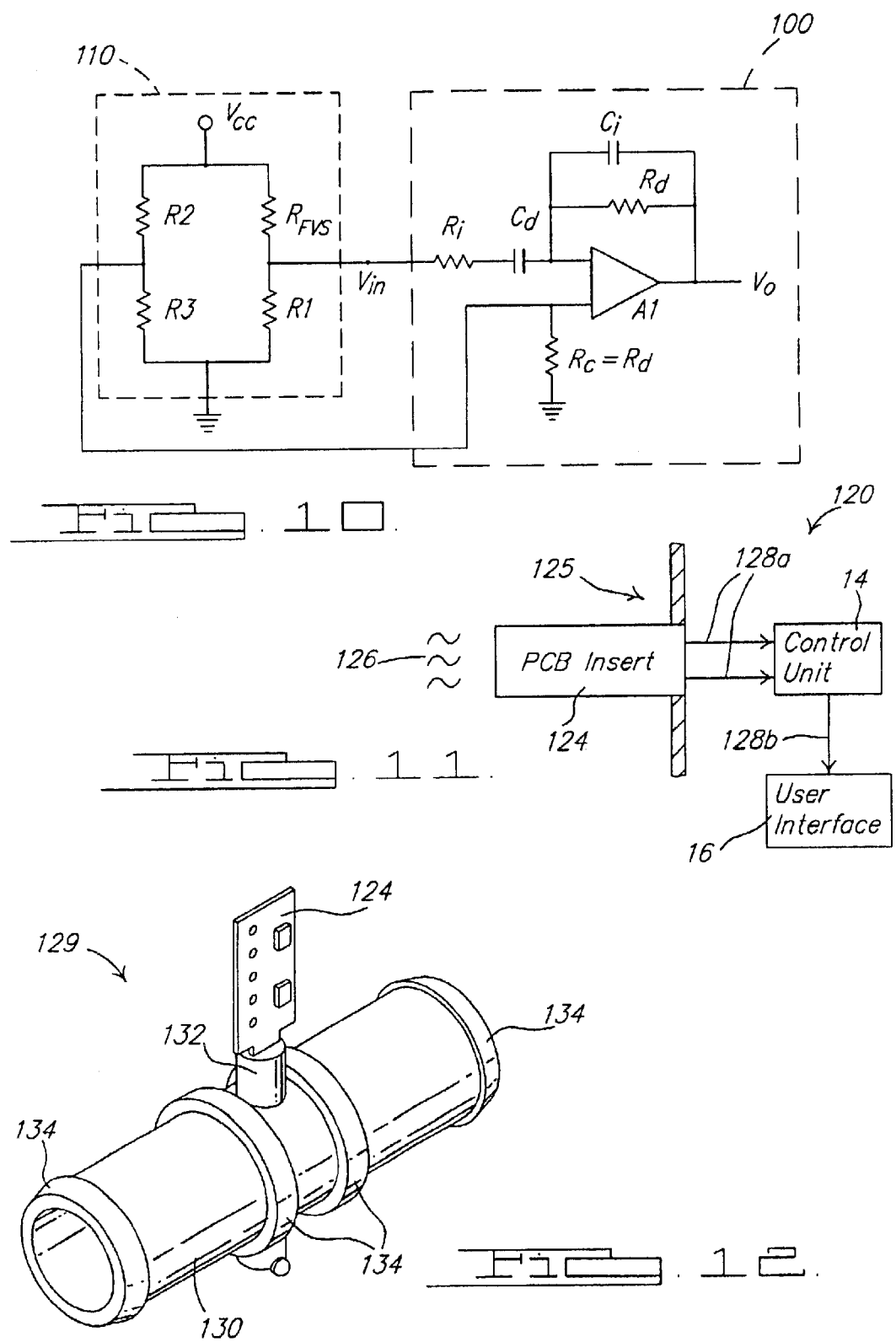

METHOD AND APPARATUS FOR THE DETECTION OF THE RESPONSE OF A SENSING DEVICE

FIELD OF THE INVENTION

The present invention generally relates to a method and apparatus for improving the detection response of a sensing device.

BACKGROUND OF THE INVENTION

Detection of specific target analytes, or chemical compounds, is important for many applications, including for example, detecting whether the concentration of analytes exceeds flammability limits. Target analytes are detected by sensors operating according to different detection mechanisms, known in the art. Most sensors employ a sensing component that is physically modified in the presence of specific analytes present in the environment. Thus, a sensor typically comprises a probe that includes both the sensing component and a probe body housing (including terminals for transmitting an output). The terminals are typically coupled to a processor, also part of the sensor, which analyzes the outputs received from the sensor probe. Such processor is coupled to a user interface, typically containing an indicating device, which signals when concentration of an analyte has exceeded threshold values.

Many sensors employ a sensing component that is a sensor film. Many sensor films swell, increasing in volume, while in the presence of the analytes. Various sensors available in the art utilize the physical changes in the sensor film to determine concentration of analyte present. Such sensors may include optical sensors, such as fiber optic sensors, where a beam of light is projected through an optical fiber at a sensor film cladding, and physical changes (e.g. refractive index or color) in the film are monitored. Such changes in refractive index occur when analytes are absorbed and change the physical properties of the cladding (including volumetric changes). Other sensors include sound acoustic wave sensors (SAWS), which project ultrasonic waves through the sensor film between transducers, and likewise detect any modifications in the properties of the sensor film (primarily the mass), translating those changes to the concentration of analyte present.

Another type of sensor film is a conductiometric sensor, more particularly, a polymer-absorption chemiresistor sensor. A polymer-absorption chemiresistor has a polymer film sensor exposed to a surrounding atmosphere containing target analytes (chemical compounds). An electrical charge is applied across the polymer film. The polymer absorbs target analytes and this results in a volumetric change of the film, and hence the electrical resistance of the film.

While current chemiresistor sensors perform adequately for their intended uses, they are subject to improvement. Specifically, the detection response of the sensor is gradual. The electrical resistance of the sensor gradually increases once the sensor film has been exposed to the analyte. This gradual increase may require a long period of time before reaching a threshold value beyond which a decision is made to turn off the machine supplying the analyte.

In one prior art detection system, the electrical resistance of a sensor gradually increases after the sensor has been exposed to the analyte. FIG. 1, illustrates an exemplary graph of a typical detection response (R vs. time) of one prior art detection system. Prior systems generally measure the electrical resistance of the sensor over a period time, which requires a long period of time before a user using the sensor is informed that the sensor has reached a threshold value $R_{th}$. As shown in this example, the threshold value of the sensor, if selected to be twice its nominal value, would result in a response time of >1400 seconds.

The detection of the flow rate of water is also important in many applications, including for example, detecting whether the amount of water being dispensed in a refrigerator icemaker exceeds overflowing limits. The flow rate of water is detected by sensors operating according to different detection mechanisms, known in the art, such as thermo-anemometers. Traditional thermo-anemometers typically include an anemometer temperature sensor disposed in a stream of water to measure the downstream temperature and a another anemometer temperature sensor disposed in the stream of water to measure the upstream temperature. The anemometer temperature sensors can be internally heated thermistors, externally heated thermistors, or other types of temperature sensors.

The anemometer sensor measuring the upstream temperature compensates for any fluctuations in water temperatures that might bias the reading of the anemometer sensor measuring the downstream temperature. The thermo-anemometer subtracts the upstream temperature from the downstream temperature to determine flow rate. By using various equations and thermal sensing principles, such as the Seebeck Effect, the temperature result is then correlated to a flow rate. Other methods can be used to measure the flow rate of water, such as, measuring the heat loss of a heat source (heat source heating the thermistors) that is exposed to the flow of the fluid and using the appropriate equations and principles to correlate the temperature measurement to a flow rate.

In an application using the prior art technology, such as the refrigerator icemaker example, the amount of water dispensed depends on line pressure, which determines the flow rate of water once the valve is opened. If the flow of water is timed, then the volume dispensed into the ice tray can vary significantly. By measuring the flow rate just after opening the icemaker dispense valve, it is possible to more accurately fill the ice tray to an appropriate level each time. However, at high flow rates of more than 0.75 GPM, the valve must only be open for a short period of time, and the measurement of flow must take place within less than 2 seconds after the valve opens. This is achieved by measuring the temperature (T) of the heat source of the thermo-anemometer over time (t), as done in the prior art. Since it takes a long period of time for the temperature (T) of the heat source to reach a steady state value, traditional thermo-anemometers are often inadequate for these applications. FIG. 2, illustrates an exemplary graph of a typical response (Temperature vs. time) of the prior art system. When temperature (T) is plotted versus time (t), the steady state value for T is not reached until 1.5 to 2.0 seconds after the water valve opens. In this example, the temperature was measured both at a flow rate of 0.15 GPM and 0.75 GPM.

There is a need for a signal conditioning technique for improving the response time of a sensing device, such as a chemiresistor sensor and a water flow sensor, thus improving the reaction response time for the user of the sensor.

SUMMARY OF THE INVENTION

In accordance with the present invention, a sensing device is provided. The sensing device comprises a sensor probe; a sensor film deposited on an end of the sensor probe, the sensor film having an electrical resistance that is adapted to change in response to the presence of a predetermined condition; means for measuring the electrical resistance of the sensor probe during a time period, and generating a first signal corresponding to the electrical resistance measurements, and differentiating the first signal, and generating a second signal corresponding to the differential of the first signal; and means for comparing the second signal with a threshold value and then generating a third signal if the second signal exceeds the threshold value.

In another aspect of the present invention the sensing device comprises: a sensor probe; an electrical component having an electrical resistance electrically connected to the sensor probe, the electrical resistance of the electrical component adapted to change in response to the presence of a predetermined condition; and a control device electrically connected to the electrical component, the control device for measuring the electrical resistance of the electrical component during a time period, and generating a first signal corresponding to the electrical resistance measurements, and determining a rate of change of the first signal, and generating a second signal corresponding to the rate of change of the first signal, and comparing the second signal with a threshold value.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 5 is a cross-sectional view taken along line 5—5 of FIG. 4;

FIG. 6 is a detailed view of an exemplary sensor film region;

FIG. 7 is a flowchart showing the operational steps of the chemiresistor sensor of the present invention;

FIG. 8 is an exemplary graph of the improved detection response of the chemiresistor sensor of the present invention;

FIG. 9 is a basic differentiator configuration of the present invention;

FIG. 10 is a 4-wire bridge differentiator circuit configuration of the present invention;

FIG. 11 is a block diagram of a water flow sensor;

FIG. 12 is a schematic illustration of an exemplary water flow sensor tube that can be used in accordance with the present invention;

DETAILED DESCRIPTION OF THE PREFERRED EMBODIMENTS

The following description of the preferred embodiments is merely exemplary in nature and is in no way intended to limit the invention, its application, or uses.

The present invention provides a signal conditioning technique for improving the response time of a sensing device. In a first configuration of a preferred embodiment, the signal conditioning technique is employed in an improved chemiresistor sensor of the present invention. Specifically, a control unit with a software program is coupled to a sensor probe of the chemiresistor sensor for directly measuring the electrical resistance from the sensor probe and determining the rate of change of the electrical resistance of the probe as the probe detects surrounding analytes. A second configuration of the preferred embodiment incorporates a basic differentiator circuit used to directly differentiate the electrical resistance of the probe. A third configuration of the preferred embodiment incorporates a 4-wire bridge differentiator circuit, which is an improvement of the basic differentiator circuit.

In an alternative preferred embodiment, the signal conditioning technique is employed in an improved water flow sensor of the present invention. Specifically, the control unit is coupled to a printed circuit board (PCB) insert of the water flow sensor for measuring the temperature of the thermistors mounted on the PCB insert, and differentiating the temperature measurements to improve the response time of the sensor. The control unit is operative to correlate the derivative of the temperature measurements into a flow rate using well known flow rate equations and principles, which are further described below. The signal conditioning technique employed in both the chemiresistor and water flow sensor of the present invention improves the detection response of the sensors, thus improving the reaction time for the user of the sensors.

Figure 1:
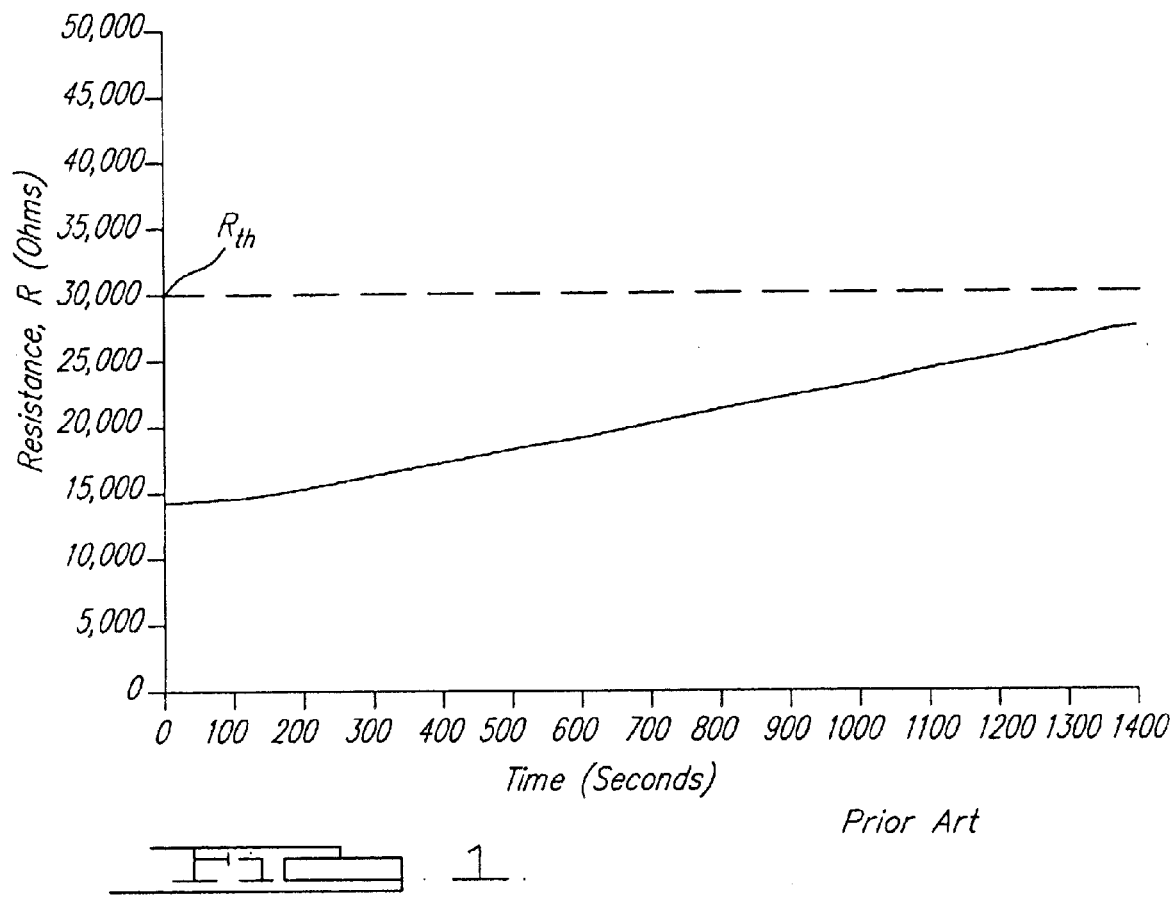
FIG. 1 is an exemplary graph of the detection response of one prior art chemiresistor sensor system.
Figure 3:
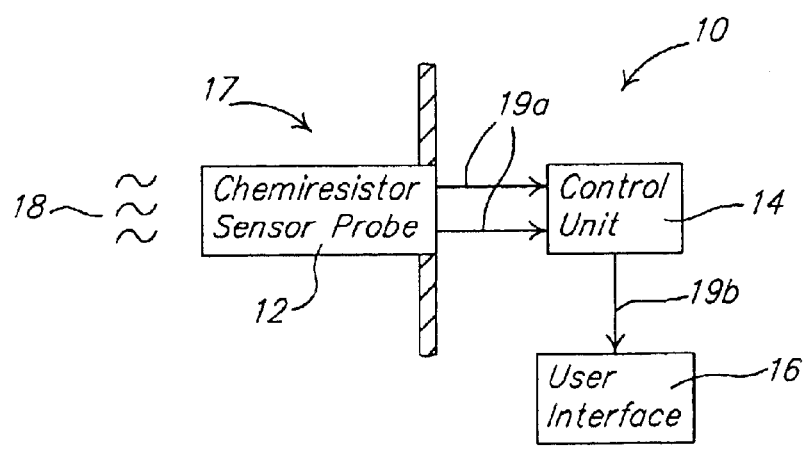
FIG. 3 is a block diagram of a chemiresistor sensor.

FIG. 3 generally depicts the major components of an exemplary chemiresistor sensor at 10. The sensor 10 is generally comprised of a chemiresistor sensor probe 12, a control unit 14, and a user interface 16. The sensor probe 12 interacts with an external environment 17 to detect the presence of analytes, or target chemical compositions 18. The sensor probe 12 generates a raw output signal 19a based on continuous detection of analytes 18 in the external environment 17. The raw output signal 19a is processed by the control unit 14. The control unit 14 transmits a calculated output signal 19b to the user interface 16 to relay analysis of the raw output signal 19a from the sensor probe 12. The user interface 16 provides information to an external user about the sensor 10 and may range from a simple alarm signal to a complex computerized screen.

Figure 4:
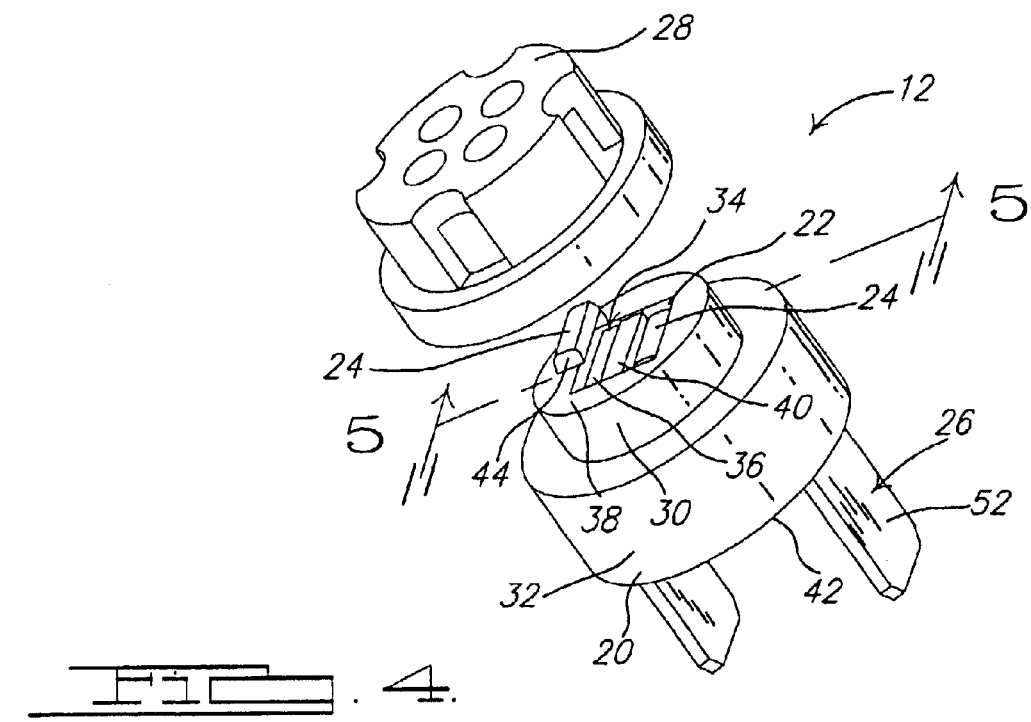
FIG. 4 is a schematic illustration of an exemplary chemiresistor sensor probe that can be used in accordance with the present invention.

Referring generally to FIG. 4, one example of a polymer-absorption chemiresistor sensor probe 12 compatible with the sensor film compositions of the teachings of the present invention is shown. The sensor probe 12 generally includes a sensor housing 20, a conductive sensor film 22 covering a portion of the sensor housing 20 (FIGS. 4 and 5), a pair of electrodes 24 are optionally disposed beneath and attached to the sensor terminals 26, and a protective cap 28. In lieu of electrodes, an alternate sensor embodiment is feasible, where the terminals 26 protrude into the sensor film 22, and serve a similar function to the electrodes 24 (i.e., deliver current through the sensor film 22).

The sensor housing 20 includes a first diameter portion 30 and a second diameter portion 32, wherein the first diameter portion is smaller in diameter than the second diameter portion. The first diameter portion 30 includes a sensing region 34. The sensing region 34 is comprised of two apertures 36 located within a first control surface 38 of the sensing region 34. Between the apertures 36 is a recessed second control surface 40 that extends across the sensing region 34. The second control surface 40 is slightly recessed below the first control surface 38.

Figure 2:
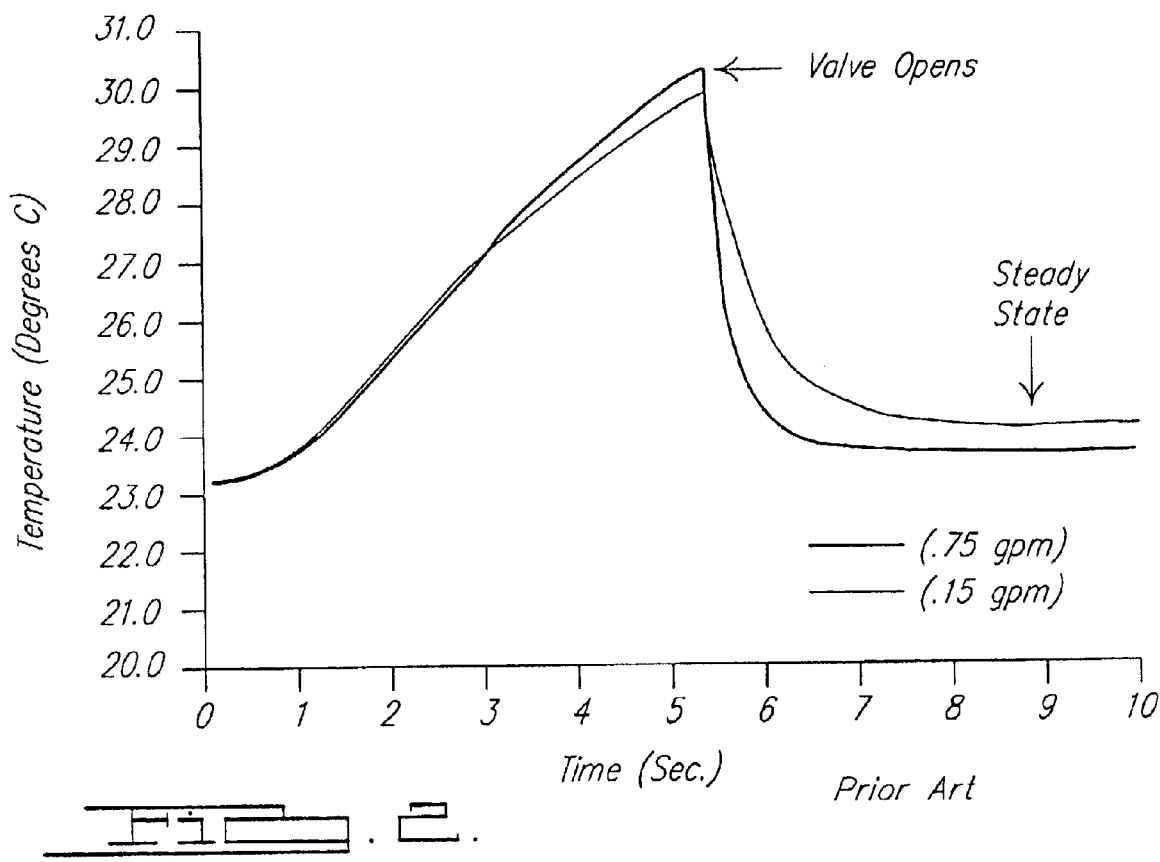
FIG. 2 is an exemplary graph of the response of one prior art water flow sensor system.

As best shown in FIG. 5, a cross-sectional view along line 5—5 of FIG. 2, each electrode 24 sits above the apertures 36. Terminals 26 are attached to the electrodes 24 and extend through both the first diameter portion 30 and the second diameter portion 32. The terminals 26 protrude from the housing 20 at an underside 42 of the second diameter portion 32. The electrodes 24 and terminals 26 are made of an electrically conductive material, preferably a metal. With specific reference to FIG. 5, the electrodes 24 each comprise a horizontal porous plate or mesh 44 that is parallel to the first control surface 38 and approximately equals the width of the aperture 36. Each electrode 24 is connected to establish an electrically conductive pathway to terminal 26. With renewed reference to FIG. 5, a first horizontal portion 46 of the terminal 26 makes either direct or indirect contact with the portion of the sensor film 22 seated within the apertures 36 to detect changes in the resistance of the sensor film 22. Extending from the first horizontal portion 46 is a first vertical portion 48. The first vertical portion 48 extends through the first diameter portion 30 and into the second diameter portion 32 where the first vertical portion 48 transitions to an inner terminal dogleg that ends in the external terminals 52 (i.e., end leads).

At the transition point between the first vertical portion 48 to the inner terminal dogleg 50, the terminals 26 have an aperture 54. The aperture 54 receives an alignment rod (not shown) during manufacturing to permit more precise alignment of the electrodes 24 within the housing 20. The use of the alignment rod during the molding process results in the formation of a through hole 56 within the underside 42 of the housing 20. The inner terminal dogleg 50 extends to the external terminals 52, which extend from the underside 42 of the second diameter portion 32. The external terminals 52 extend from the housing 20 to a suitable length to permit interconnecting the leads to a corresponding outlet (not shown) of a suitable alert device, such as an alarm.

As best seen in FIG. 6, detailed view of the sensing region 34 from FIGS. 4 and 5, the sensor film 22 comprises a polymer 60 with conductive particles 62 dispersed throughout. The terminals 26 extend through a body 64 of the sensor probe housing 20 and are electrically connected to the electrodes 24. The electrodes 24 protrude into the sensing region 34 and into the sensor film 22. The electrodes 24 preferably are situated near the surface, and further across the sensor film, for even current distribution. A preferable configuration of the sensor film 22 includes electrically conductive particles 62 distributed homogeneously (e.g. evenly) throughout the sensor film 22 body forming an electrically conductive polymeric matrix 66. "Matrix" refers generally to a polymer system having filler particles distributed throughout within the polymer.

The conductive sensor film matrix 66 is seated upon the first control surface 38 such that the matrix 66 fills the apertures 36 and spans the center control surface 40. The matrix 66 fills the apertures 36 so that the matrix 66 is in either direct or indirect electrical contact with both of the electrodes 24. Upon exposure of the matrix 66 to target analytes, the matrix 66 volume increases by swelling.

The polymer 60 of the sensor film 22 can be any polymer that readily absorbs a target analyte or chemical compound, through a gas-solid interface occurring between a surface of the sensor film 22 and the surrounding gas in the external environment 17 (FIG. 3) at a rate that is relatively proportional to the concentration of the analyte in the surrounding gas. Thus, a correlation can be made between the quantity of analyte absorbed, and the concentration of the analyte in the surrounding gas. In the exemplary sensor probe 12 depicted, the change in the volume of the sensor film 22 is correlated to the concentration of the analyte present in the gas and is further related to the resistance of the sensor film 22. Of particular interest is the length of time, known as the detection response time, in which a user of the sensor can be informed of the presence of the analyte 18. A number of signal conditioning techniques are contemplated in the present invention, and further discussed below.

It is preferred that the sensor film consists of a carbon-black filled silicone, which swells in the presence of analytes. The increase in the resistance of the sensor film is thus dependent on the swelling properties of the carbon black filled silicone. It should be understood that various types of polymers may be used in the present invention, such as, for example, siloxane-based polymers.

Referring back to FIG. 3, a first configuration of the preferred embodiment is shown. The sensor probe 12 is coupled to the control unit 14. The control unit 14 measures and processes the raw output signal 19a, representative of the electrical resistance of the sensor, from the sensor probe 12. The user interface 16 is coupled to the control unit 14 for displaying the detection response (defined as resistance R, or its derivative dR/dt versus time), measured by the control unit 14 graphically or numerically. The user interface 16 can be any suitable interface, such as, for example, a computer monitor. However, as mentioned, any indicating device, such as, for example, a buzzer or a red light may be employed to inform the user of the sensor the presence of analyte 18 or whether the concentration of the analyte 18 has exceeded the threshold. It should be understood that the control unit 14 may be any suitable processor well known in the art.

FIG. 7 is a flowchart showing the operational steps of the chemiresistor sensor 10. The chemiresistor starts in step 80. In step 82, the sensor probe 12 detects analyte 18. In step 84, the control unit 14 measures the electrical resistance R of the sensor probe 12. Next, the control unit 14 numerically differentiates (dR/dt) the electrical resistances measured from the sensor probe 12 by taking successive points off of the electrical resistance measurements, subtracting one from the other, then dividing the resistance difference into the time difference between successive points in step 86. Finally, the user interface 16 displays the calculated results, representative of the derived resistance measurements, sent by the control unit 14 to inform the user of the sensor 10 the presence of the analyte 18 in step 88. The processing from steps 82 to 88 is continuous. The duration of each loop (sequence of steps 82–88) depends on the processing capabilities of control unit 14. These capabilities include, among others, its speed and resolution.

In addition to measuring and differentiating the electrical resistances done in steps 84 and 86, the control unit 14 is also capable of comparing the differentiated electrical resistance measurements to a threshold value. The threshold value is a predetermined value representing an amount of target analytes 18 considered to be harmful to the system in which the sensor 10 is employed. As such, the user of the sensor 10 will be informed when the differentiated electrical resistance measurements exceed the threshold value. Alternatively, the control unit 14 will automatically shut down the sensor 10 or the entire system when the differentiated electrical resistance measurements exceed the threshold value.

Referring now to FIG. 8, an exemplary graph of the detection response of chemiresistor sensor 10 using the differentiation technique as described above is shown. Taking the numerical derivative of the electrical resistance measurements taken from by the control unit 14 allows sensor 10 to provide a steady state response within a short amount of time (in this example, ~200 seconds from the time the sensor probe 12 detected the analyte 18 to the time the sensor probe 12 reaches a threshold value). A threshold level for dR/dt can be chosen accordingly (in this case, 8.0 ohms/sec, for example) at which point an alarm would be triggered. This real-time differentiation technique will generally result with at least an order of magnitude improvement in the detection response time of the sensor 10. While a time of ~200 seconds is disclosed, it should be understood the detection response time can further be improved by using different types of sensors.

In a second configuration of the preferred embodiment, the sensor probe 12 incorporates a basic differentiator circuit 100 as shown in FIG. 9. The differentiator circuit 100, as well known in the art, generates an output voltage that is proportional to the rate at which the input voltage is changing. The sensor probe 12 is represented as a resistor $R_{FVS}$. Resistor $R_{FVS}$ is coupled in series with a fixed resistor $R_1$ and a voltage supply $V_{cc}$. Resistor $R_{FVS}$ and resistor $R_1$ are coupled in parallel with the differentiator circuit 100.

The differentiator circuit 100 generally comprises an operational-amplifier (op-amp) 102, fixed resistors $R_i$, $R_d$, and $R_c$, and fixed capacitors $C_d$ and $C_i$. The op-amp 102 includes input terminals 104a, 104b that constitute a differential input. Terminal 104a is marked with a minus sign and is normally called the negative terminal. Terminal 104b is marked with a positive sign and is normally called the positive terminal. The terminals 104a, 104b are both defined as positive with respect to ground. Terminal 104b is connected to resistor $R_c$. Resistor $R_c$ is coupled to ground, thereby providing a path to ground for a current from op-amp 102. The op-amp 102 further includes an output terminal 106 with a single-ended output voltage $V_o$. It should be understood that the upper terminal may be the positive input terminal and the lower negative, depending on the application.

In operation, the sensor probe 12 detects analyte 18, increasing the electrical resistance of the sensor probe 12. The increase in the electrical resistance of the sensor probe 12 causes the value of the input voltage $V_{in}$ of the op-amp 102 to change according to the following equation:

$$V_{in}=V_{cc}*(R_1/(R_1+R_{FVS}))$$

The input voltage $V_{in}$ varies as the electrical resistance of the sensor probe 12 changes. Thus, the electrical resistance of the sensor probe 12 is a function of the input voltage $V_{in}$ of the differentiator circuit 100.

The output voltage $V_o$ of the op-amp 102 will be approximately equal to:

$$V_o \approx -R_d*C_d*(dV_{in}/dt)$$

The output voltage $V_o$ of the op-amp 102 is also a function of the electrical resistance of the sensor probe 12. The output voltage $V_o$ is calculated by taking the derivative of the input voltage $V_{in}$ and multiplying it by the negative value of resistor $R_d$ and the value of capacitor $C_d$. The input voltage $V_{in}$ and the output voltage $V_o$ are both dependent on the changes in the electrical resistance of the sensor probe 12, which correlate to the concentration of analyte 18. Slight changes in the electrical resistance of the sensor probe 12 will impact the input voltage $V_{in}$ and hence the output voltage $V_o$. The differentiator circuit 100 is another way of improving the detection response time of the sensor 10. It should be understood that the differentiator circuit 100 can be implemented as described above or accomplished strictly through software embedded in control unit 14.

In a third configuration of the preferred embodiment, the differentiation circuit 100 is incorporated into a 4-wire bridge circuit 110 as shown in FIG. 10. The 4-wire bridge circuit 110 comprises resistors $R_1$, $R_2$, $R_3$ and $R_{FVS}$. Resistor $R_{FVS}$ represents the electrical resistance of the sensor probe 12. The 4-wire bridge circuit 110 is used so that the output voltage $V_o$ is not affected by the fluctuations of the voltage supply $V_{cc}$, which may occur. In such a case, the input voltage $V_{in}$ will change according to the following equation:

$$V_{in}=V_{cc}*[(R_1/(R_1+R_{FVS}))-(R_3/(R_2+R_3))]$$

Thus, if the ratio of $(R_1(R_1+R_{FVS}))$ is chosen to be approximately equal to $(R_3/(R_2+R_3))$, the input voltage $V_{in}$ and the output voltage $V_o$ will be desensitized to small changes in $V_{cc}$.

In an alternative embodiment, the sensor probe 12 may comprise a self-contained unit that produces a digital output indicative of the satisfying of a predetermined condition, such as the presence of target analyte in a specific concentration. In this regard, the sensor probe 12', itself, incorporates any hardware and/or software that may be necessary for measuring the electrical resistance of the sensor film over time, determining the rate of change in the electrical resistance measurements, comparing the rate of change to a predetermined threshold value, and generating a corresponding output. The hardware and/or software that may be incorporated into the sensor probe 12' generally can include a measurement module, a differentiator, a comparator, and a signal generator. The measurement module performs the function of measuring the electrical resistance of the sensor film over time, the differentiator is used for determining the rate of change of the electrical resistance measurements, the comparator is used for comparing the differential to the threshold value, and the signal generator generates the corresponding output. In a sensor including such a sensor probe 12', the sensor probe 12' is in direct communication with the user interface 16. Consequently, the sensor probe 12' may be operative to provide an output directly to the user interface 16 that is indicative of whether the predetermined condition that the sensor probe 12' is being used to measure has, in fact, exceeded the threshold value. It should be understood that the functions of measuring, differentiating, comparing, and generating may also be performed by some combination of both the sensor probe 12' and the control device 14.

In an alternative preferred embodiment the signal conditioning technique is employed in a water flow sensor 120. FIG. 11 generally depicts the major components of an exemplary water flow sensor at 120. The water flow sensor 120 generally comprises a Printed Circuit Board (PCB)

insert 124, a control unit 14, and a user interface 16. Both the chemiresistor sensor 10 and the water flow sensor 120 employ control unit 14 and user interface 16. The PCB insert 124 is typically disposed in an environment of water 125 to detect the flow rate of water 126. The PCB insert 124 generates an output signal 128a based on continuous detection of the flow rate of water 126 in the environment of water 125. The output signal 128a is processed by the control unit 14. The control unit transmits a calculated output signal 128b to the user interface 16 to relay analysis of the output signal 128a from the PCB insert 124. The user interface 16 provides information to the external user about the water flow sensor 120 and may range from a simple alarm signal to a complex computerized screen.

Referring generally to FIG. 12, an exemplary embodiment of a water flow sensor tube 129 enclosing the PCB insert 124 of the present invention is shown. The water flow sensor tube 129 generally comprises a first and second housing 130, 132 respectively. The first housing 130 typically is in the shape of a annular cylindrical tube having annular flanges 134 and adapted to receive the flow of water 126. The annular flanges 134 serve for connection purposes, for example, connection to a water valve through flexible hoses. The second housing 132 is typically a thermally conductive plastic flow tube that encloses/encapsulates the PCB insert 124, protecting the components of the PCB insert 124 from moisture and corrosion. It should be understood that the first and second housing 130, 132 respectively can be made up of various types of thermally conductive polymers, such as, for example, polypropelene, polyvinylchloride, polyacetylene, polyparaphenylene, polypyrrole, and polyaniline. Mineral and/or glass fillers mixed in with these base polymers have shown to greatly enhance the material's thermal conductivity. One such material is Konduit MT-210-14 from GE/LNP.

Figure 13:
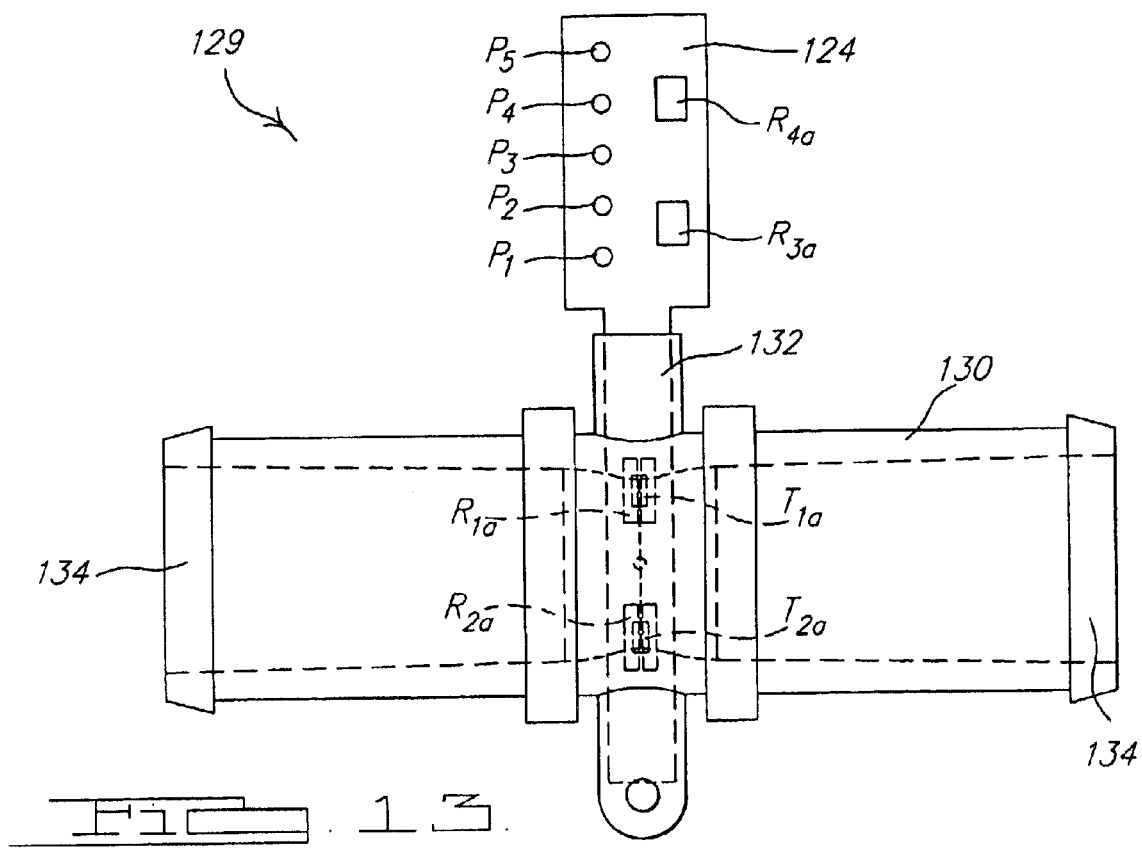
FIG. 13 is a cross-sectional view of FIG. 12.
Figure 14:
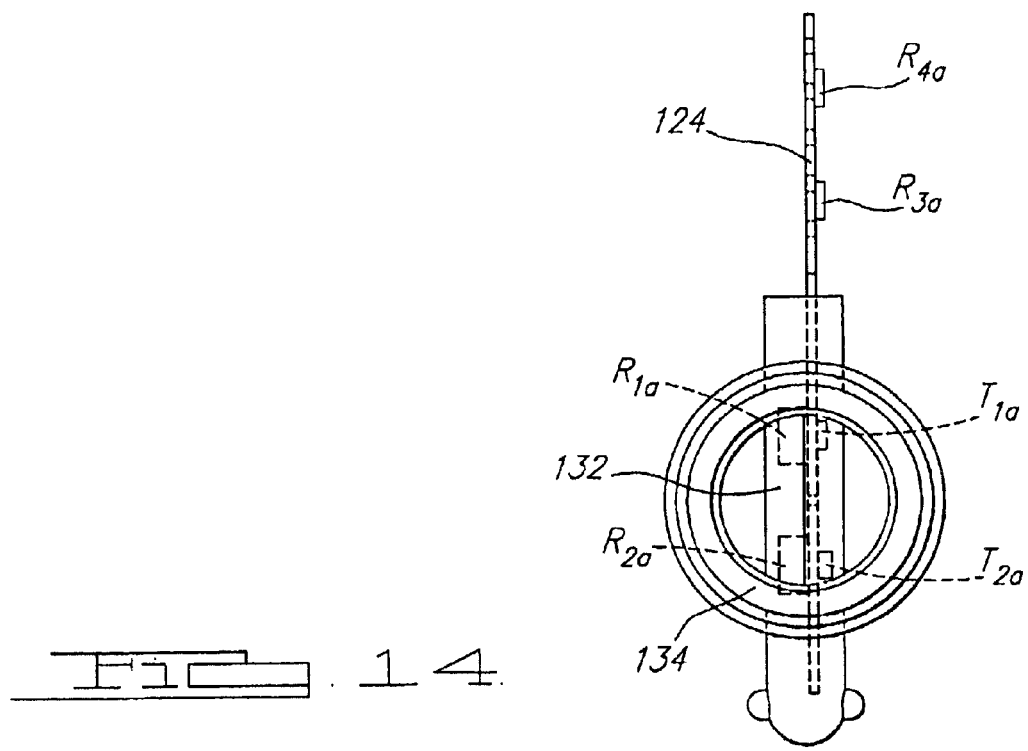
FIG. 14 is a front view of the water flow sensor tube.
Figure 15:
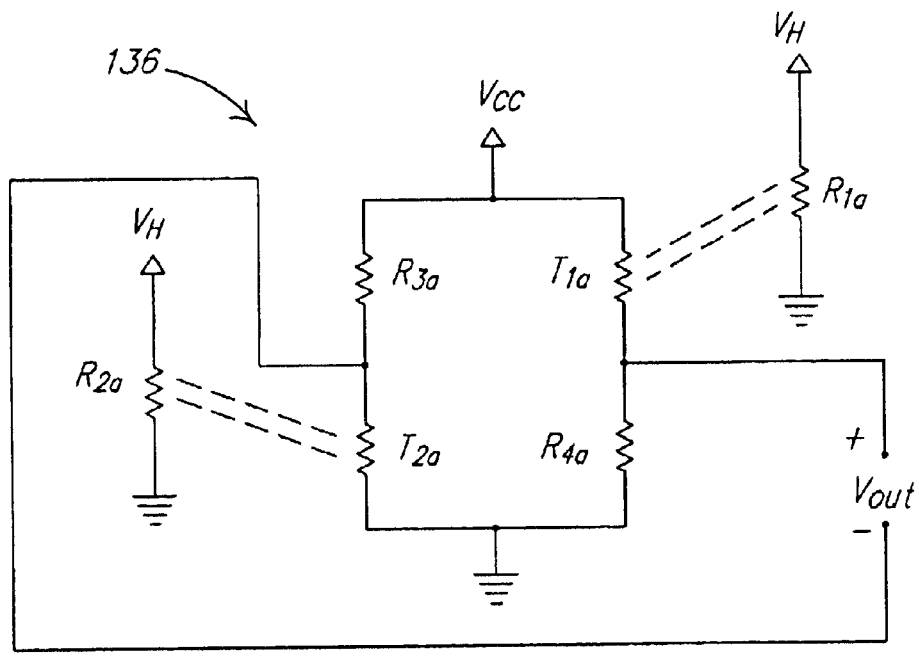
FIG. 15 is the circuit diagram of a printed circuit board insert of the water flow sensor.

Referring generally to FIGS. 13–15, details of the PCB insert 124 of the present invention are shown. The PCB insert 124 generally includes an upper and lower portion that comprise a bridge circuit 136. The bridge circuit 136 generally comprises heating resistors $R_{1a}$, $R_{2a}$, fixed bridge resistors $R_{3a}$, $R_{4a}$, thermistors $T_{1a}$, $T_{2a}$, I/O pins $P_1$, $P_2$, $P_3$, $P_4$, $P_5$, a voltage source $V_{CC}$, and a heater voltage source $V_H$. Specifically, the lower portion of the PCB insert 124, which is subjected to water flow 126, includes thermistors $T_{1a}$, $T_{2a}$ and heating resistors $R_{1a}$, $R_{2a}$. The upper portion of the PCB insert 124 includes fixed bridge resistors $R_{3a}$, $R_{4a}$ and I/O pins $P_1$, $P_2$, $P_3$, $P_4$, $P_5$. It should be understood that the number of thermistors and heater resistors may vary depending on the application. As an example, thermistor $T_{2a}$ could be replaced with a fixed resistor, and heater resistor $R_{2a}$ could be omitted in applications where improved sensitivity is not required. Furthermore, heater resistor(s) $R_{1a}$ (and/or $R_{2a}$) and voltage source $V_H$ may be omitted in applications where thermistor(s) $T_{1a}$ (and/or $T_{2a}$) can be internally self-heated.

Referring to FIG. 13, the PCB insert 124 is generally disposed perpendicular with respect to the fluid flow direction going through the first housing 130 and within the second housing 132. The top portion of the PCB insert 124 extends slightly above the second housing 132 and an intermediate portion of the lower portion of the PCB insert 124 extends slightly below the first housing 130. The first housing 130 is adapted to receive a flow of water 126, which in turn, flows past the second housing 132. The cross-sectional shape of housing 132 may be shaped such that water vortexes (and associated detrimental impact on heat transfer) are minimized or eliminated.

Referring generally to FIG. 15, an exemplary bridge circuit configuration 136 of the components of the PCB insert 124 is shown. Resistor $R_{3a}$ is coupled in series with thermistor $T_{2a}$ and voltage source $V_{CC}$. Thermistor $T_{1a}$ is coupled in series with resistor $R_{4a}$ and voltage source $V_{CC}$. Together, resistor $R_{3a}$ and thermistor $T_{2a}$ are coupled in parallel with thermistor $T_{1a}$ and resistor $R_{4a}$. Heating resistor $R_{1a}$ is energized by supply voltage $V_H$ and provides heat to thermistor $T_{1a}$. Heating resistor $R_{2a}$ is also energized by supply voltage $V_H$ and provides heat to thermistor $T_{2a}$. Independent leads are coupled to each thermistors $T_{1a}$, $T_{2a}$ to provide an output voltage $V_{out}$, representative of the potential voltage difference between the two legs of the 4-wire bridge circuit. In this example, pin $P_1$ and $P_2$ are the leads in which the output voltage $V_{out}$ is measured from. Pin $P_3$ provides voltage $V_H$ to heating resistors $R_{1a}$, $R_{2a}$. Pin $P_4$ goes to the voltage supply $V_{cc}$ of the bridge circuit 136. Pin $P_5$ is connected to ground.

In a first configuration of the alternative preferred embodiment, the PCB insert 124 is coupled to control unit 14 as shown in FIG. 11. Specifically, leads coming from pins $P_1$ and $P_2$ of the PCB insert 124 are coupled to the control unit 14. The control unit 14 is used to measure and analyze the output signal 128a, representative of the heat loss of thermistors $T_{1a}$, $T_{2a}$ based on the flow rate of water 126. The user interface 16 is coupled to the control unit 14 for displaying the response measured by the control unit 14 graphically or numerically.

Figure 16:
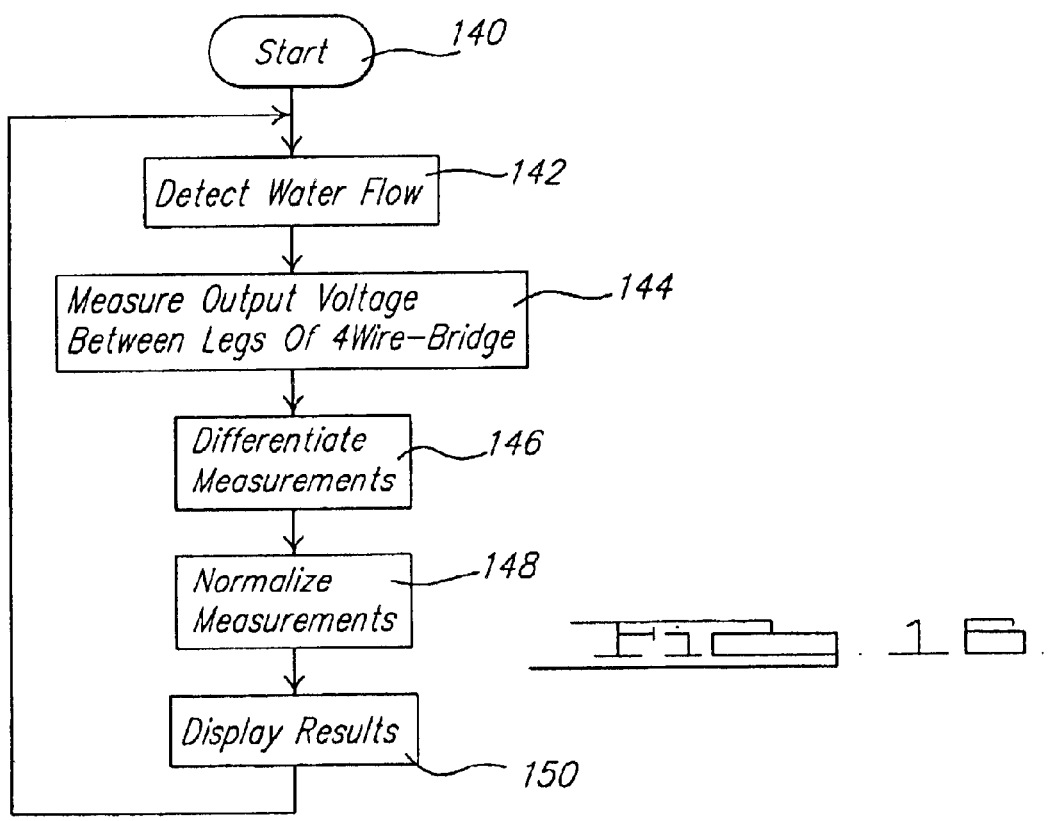
FIG. 16 is a flow chart showing the operational steps of the water flow sensor.

FIG. 16 is a flowchart showing the operational steps of the water flow sensor 120. The water flow sensor starts in step 140. In this step, thermistor $T_{1a}$ and $T_{2a}$ are heated by heating resistors $R_{1a}$, $R_{2a}$ and voltage source $V_H$ for a finite period of time causing the temperature of thermistors $T_{1a}$ and $T_{2a}$ to rise. In step 142, the PCB insert 124 detects the flow of water 126 flowing through the water sensor flow tube 129, decreasing the temperature of thermistors $T_{1a}$ and $T_{2a}$. The output voltage $V_{out}$ measured between the two legs of the 4 wire bridge is measured in step 144. Next, the control unit 14 differentiates ($dV_{out}/dt$) the output voltage measurements, representative of the temperature of thermistors $T_{1a}$ and $T_{2a}$, by taking successive points off of the output voltage measurements, subtracting one from the other, and dividing the output voltage difference $dV_{out}$ by the time interval dt between successive measurements in step 146. In step 148, the control unit 14 normalizes the temperature measurements and converts them into a flow rate. Finally, the user interface 16 displays the flow rate of the detected water 126 in step 150. The processing from steps 140 to 150 is continuous. The duration of each loop (Sequence of steps 142–150) depends on the processing capabilities of control unit 14. These capabilities include, among others, its speed and resolution.

In the above example, the differential output voltage (Vout) of circuit bridge 136 is correlated to the thermistors' resistance value ($R_{ntc}$) according to the following equation:

$$R_{ntc} = R_{fixed} * (V_{cc} - V_{out}) / (V_{cc} + V_{out})$$

It is assumed that both thermistors are at the same temperature $T = T_{1a} = T_{2a}$, and that $R_{3a} = R_{4a} = R_{fixed}$. The temperature value (T) in degrees Kelvin is calculated according to the following equation:

$$T = (1/T_o + ln(R_{ntc}/R_o)/\beta)^{-1}$$

Where temperature $T_o = 298.15°$ K., $R_o$ is the thermistors' resistance at temperature $T_o$, and $\beta$ is an intrinsic parameter indicative of the temperature sensitivity of the thermistor.

The temperature value (T) measurements are then differentiated and normalized by the control unit 14 as described above. It should be understood that the bridge circuit 136 can be evaluated using various equations and principles well known in the art. More specifically, heat transfer theory predicts that as soon as the water flow starts, the thermistor temperature T begins to drop sharply. It can be shown that the temperature drop is exponential, namely it can be expressed as:

$$T - T_{final} = (T_{start} - T_{final}) \exp(-Kt)$$

Where $T_{start}$ is the temperature at the beginning of the water flow, $T_{final}$ is the final steady state temperature with the water flow, and t is the time after the flow starts. K in Eg. (1) represents the cooling rate by the water and is considered to be a measure of the sensor sensitivity. Since the sensor is cooled convectively by the flow, K is proportional to the square-root of the flow rate.

In terms of temperature change with time (dT/dt), the minimum value occurs soon after the start of the water flow. From the equation above, the maximum value is shown to be proportional to K ($T_{start} - T_{final}$). The temperature drop ($T_{start} - T_{final}$) slightly increases with the flow rate. If we neglect the difference in ($T_{start} - T_{final}$), the sensitivity of the sensor increases with K, which means that the sensitivity changes roughly as the square-root of the flow rate.

Figure 17:
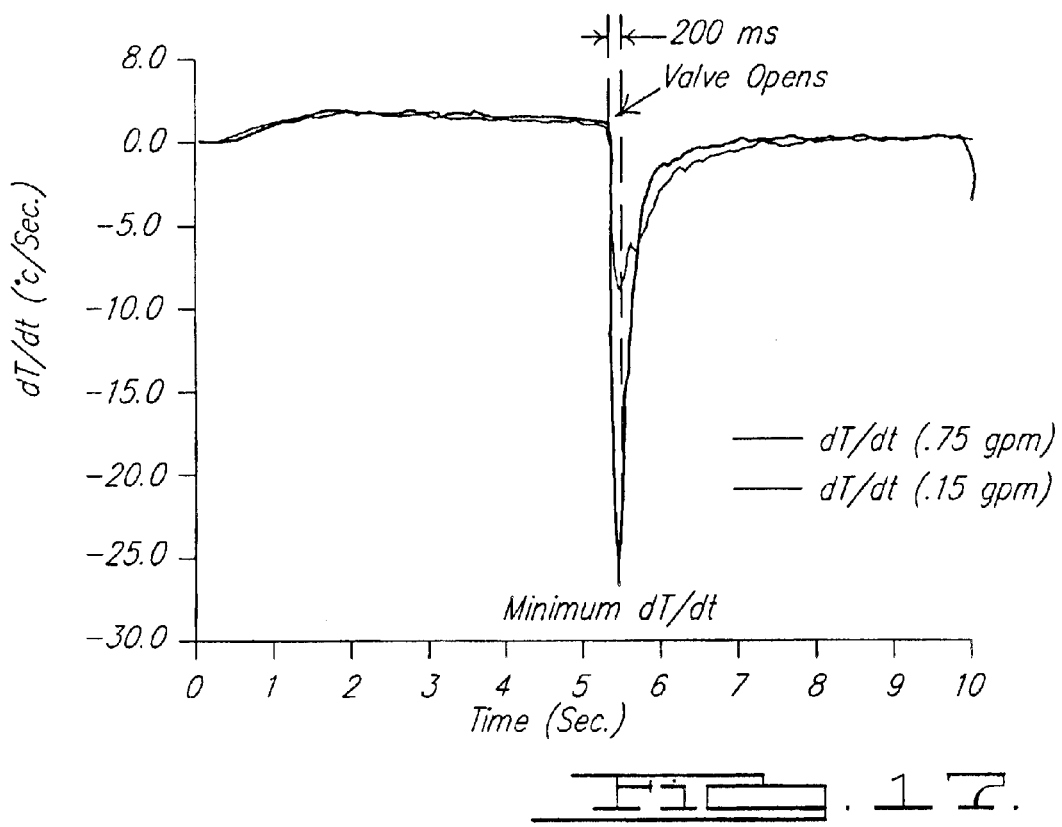
FIG. 17 is an exemplary graph of the improved response of the water flow sensor of the present invention.
Figure 18:
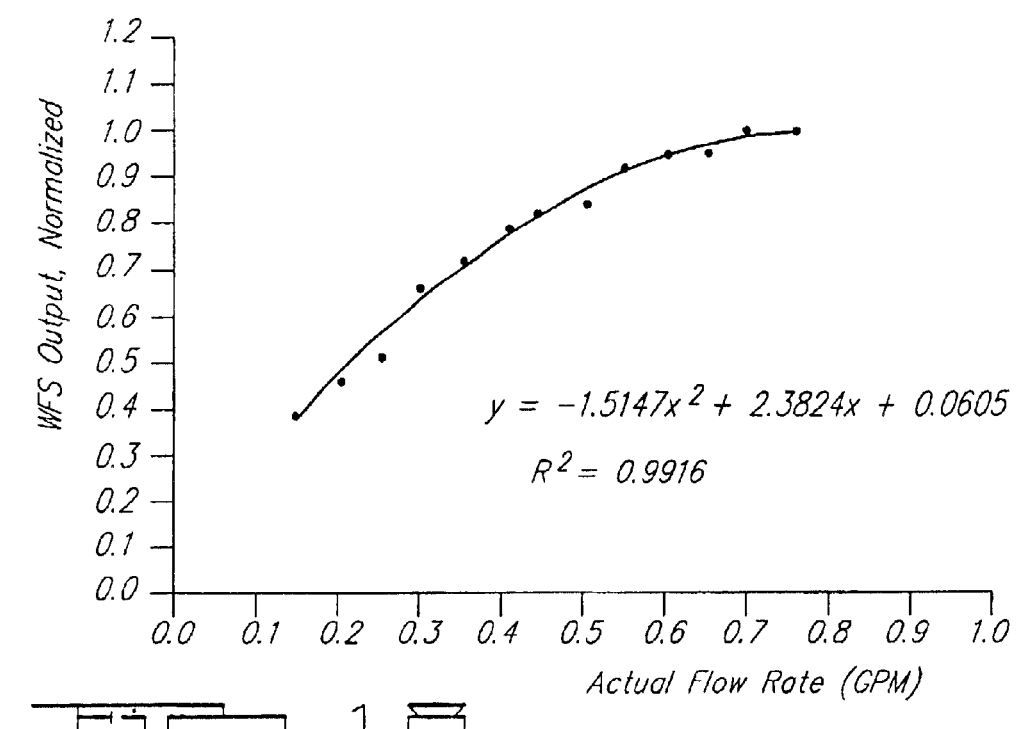
FIG. 18 is an exemplary graph of normalized flow sensor response versus actual flow rate.

Referring now to FIG. 17, an exemplary graph of the response of the water flow sensor 120 applied in the refrigerator icemaker example is shown. Taking the numerical derivative of the temperature measurements taken by the control unit 14 allows the water flow sensor 120 to reach a minimum dT/dt within a short amount of time (in this example, about 200 ms after the valve opens). This is one-tenth the time it took for temperature (T) in the prior art to reach a steady state value. The differentiation technique will generally result in an order of magnitude improvement in the response time of water flow sensor 120. While a time of about 200 ms is disclosed, it should be understood that the response time can further be improved by using different types of sensors. The minimum dT/dt is normalized to calibrate the water flow sensor versus actual water flow rates as shown in FIG. 18. The process involves: generating characteristic curves of dT/dt versus time at various flow rates (in this case N=13); capturing the minimum dT/dt at each flow rate; and dividing the minimum dT/dt at each flow rate by the minimum dT/dt at the highest flow rate expected in the application.

It should be understood that multiple configurations of the alternative embodiment are envisioned, such as, for example, employing a basic differentiator circuit or a 4-wire bridge circuit to the water flow sensor as done with the chemiresistor sensor.

Although the differentiating operation, discussed above, was in the context of the first order derivative, it should further be understood that higher order derivatives of the output signal of the sensor may be produced. Computation of such higher order derivatives is believed to further improve the response time of the sensor system.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for operating a sensing device comprising:
   providing a sensor having an electrical resistance that is adapted to change in response to a predetermined condition;
   measuring the electrical resistance of the sensor at a first time;
   measuring the electrical resistance of the sensor at a second time;
   determining a rate of change of the electrical resistance between the first time and the second time; and
   comparing the rate of change of the electrical resistance against a threshold value.

2. The method of claim 1, further comprising:
   generating a signal to a control device if the rate of change of the electrical resistance exceeds the threshold value; and
   operating an indicating device when the rate of change of the electrical resistance exceeds the threshold value.

3. The method of claim 2, further comprising displaying the comparison results on a computer monitor in at least one of a graphical and numerical manner.

4. The method of claim 2, further comprising alerting the user of the sensing device in at least one of a visual and audio signal.

5. The method of claim 1, wherein providing a sensor having an electrical resistance that is adapted to change in response to a predetermined condition comprises providing a sensor film comprising a matrix of a plurality of carbon black filled silicone.

6. The method of claim 1, wherein providing a sensor having an electrical resistance that is adapted to change in response to a predetermined condition comprises providing a sensor having an electrical resistance that is adapted to change in response to the presence of a target analyte.

7. The method of claim 1, further comprising determining the $n^{th}$ order derivative of the rate of change, where $n \geq 1$.

8. A method for operating a sensing device comprising:
   providing a sensor probe having an electrical resistance that is adapted to change in response to the presence of a target analyte;
   measuring the electrical resistance of the sensor probe at a first time;
   measuring the electrical resistance of the sensor probe at a second time;
   sending signals representing the electrical resistance measurements to a control device; and
   determining a rate of change of the signals with the control device.

9. The method of claim 8, further comprising:
   comparing the rate of change of the signal against a threshold value with the control device; and
   operating an indicating device when the rate of change of the signal exceeds the threshold value.

10. The method of claim 9, further comprising alerting the user of the sensing device with at least one of a visual and audio signal.

11. The method of claim 9, further comprising controlling an appliance when the rate of change of the signal exceeds the threshold value.

12. The method of claim 9, further comprising determining the $n^{th}$ order derivative of the rate of change, where $n \geq 1$.

13. A method for operating a sensing device comprising:
   providing a sensor probe comprising a sensor film having an electrical resistance that is adapted to change in response to the presence of a target analyte;
   measuring the electrical resistance of the sensor film at a first time;
   measuring the electrical resistance of the sensor film at a second time;
   determining a rate of change of the electrical resistance between the first time and the second time; and generating a signal representing the rate of change of the electrical resistance measured between the first and second time.

14. The method of claim 13, further comprising:
sending the signal to a control device; and
comparing the signal to a threshold value with the control device.

15. The method of claim 14, further comprising:
informing a user of the sensing device when the signal exceeds the threshold value; and
controlling an appliance when the signal exceeds the threshold value.

16. The method of claim 13, further comprising determining the $n^{th}$ order derivative of the rate of change, where $n \geq 1$.

17. A method for operating a sensing device comprising:
providing an electrical component having an electrical resistance adapted to change in response to the presence of a flow of a fluid;
measuring the electrical resistance of the electrical component at a first time;
measuring the electrical resistance of the electrical component at a second time; and
determining a rate of change of the electrical resistance between the first time and the second time.

18. The method of claim 17, further comprising:
determining a flow rate of the fluid based on the rate of change of the electrical resistance; and
comparing the flow rate of the fluid against a threshold value.

19. The method of claim 18, further comprising:
generating a signal to a control device when the flow rate of the fluid exceeds the threshold value; and
informing a user of the sensing device when the control device receives the signal.

20. The method of claim 19, further comprising controlling an appliance when the control device receives the signal.

21. The method of claim 17, wherein providing an electrical component having an electrical resistance adapted to change in response to the presence of a flow of a fluid comprises providing a thermistor adapted to change in electrical resistance in response to a change in temperature.

22. The method of claim 17, further comprising determining the $n^{th}$ order derivative of the rate of change, where $n \geq 1$.

23. A sensor comprising:
a sensor film having an electrical resistance that is adapted to change in response to the presence of a predetermined condition;
means for measuring the electrical resistance of the sensor film during a period of time;
means for generating a first signal corresponding to the electrical resistance measurements;
means for differentiating the first signal;
means for generating a second signal corresponding to the differential of the first signal; and
means for comparing the second signal with a threshold value and generating a third signal when the second signal exceeds the threshold value.

24. The sensor of claim 23, further comprising:
means for displaying the comparison results to a user of the sensor; and
means for controlling an appliance when the third signal is generated.

25. The sensor of claim 24, wherein the means for displaying the comparison results to a user of the sensor is a computer monitor.

26. The sensor of claim 23, wherein the sensor is a chemiresistor sensor.

27. The sensor of claim 23, wherein the sensor film is a matrix comprising a plurality of carbon black filled silicone.

28. The sensor of claim 23, further comprising means for determining the $n^{th}$ order derivative of the second signal, where $n \geq 1$.

29. A sensing device comprising:
a sensor probe;
an electrical component having an electrical resistance electrically connected to the sensor probe, the electrical resistance of the electrical component adapted to change in response to the presence of a predetermined condition; and
a control device electrically connected to the electrical component, the control device for measuring the electrical resistance of the electrical component during a time period, and generating a first signal corresponding to the electrical resistance measurements, and determining a rate of change of the first signal, and generating a second signal corresponding to the rate of change of the first signal, and comparing the second signal with a threshold value.

30. The sensing device of claim 29, wherein the control device further is operative to control an appliance when the second signal exceeds the threshold value.

31. The sensing device of claim 29, further comprising an indicating device for informing a user when the second signal exceeds the threshold value.

32. The sensing device of claim 29, wherein the electrical component is a sensor film.

33. The sensing device of claim 32, wherein the sensor film is a matrix comprising a plurality of carbon black silicone.

34. The sensing device of claim 29, wherein the predetermined condition is the presence of a target analyte.

35. The sensing device of claim 29, wherein the electrical component is a thermistor having a temperature adapted to change based on the presence of the predetermined condition.

36. The sensing device of claim 35, wherein the predetermined condition is a rate of flow of a fluid.

37. The sensing device of claim 29, wherein the electrical component is encapsulated by a thermally-conductive polymer.

38. The sensing device of claim 29, wherein the control device is further used for determining the $n^{th}$ order derivative of the second signal, where $n \geq 1$.

39. A sensor probe comprising:
an electrical component having an electrical resistance electrically connected to the sensor probe, the electrical resistance of the electrical component adapted to change in response to the presence of a predetermined condition;
a measurement module that measures the electrical resistance of the electrical component during a time period and generates a first signal corresponding to the electrical resistance measurements;
a differentiator that determines a rate of change of the first signal and generates a second signal corresponding to the differential of the first signal; and
a comparator that compares the second signal with a threshold value.

40. The sensor probe of claim 39, further comprising a control device that controls an appliance when the second signal exceeds the threshold value.

41. The sensor probe of claim 39, further comprising an indicating device that informs a user when the second signal exceeds the threshold value.

42. The sensor probe of claim 39, wherein the electrical component is a sensor film.

43. The sensor probe of claim 42, wherein the sensor film is a matrix comprising a plurality of carbon black silicone.

44. The sensor probe of claim 39, wherein the predetermined condition is the presence of a target analyte.

45. The sensor probe of claim 39, wherein the electrical component is a thermistor having a temperature adapted to change based on the presence of the predetermined condition.

46. The sensor probe of claim 45, wherein the predetermined condition is a rate of flow of a fluid.

47. The sensor probe of claim 39, wherein the electrical component is encapsulated by a thermally-conductive polymer.

48. The sensor probe of claim 39, wherein the differentiator further determines the $n^{th}$ order derivative of the second signal, where $n \geq 1$.

\* \* \* \* \*